United States Patent [19]

Chou et al.

[11] Patent Number: 5,274,172
[45] Date of Patent: Dec. 28, 1993

[54] PREPARING GRANULAR ESTERS

[75] Inventors: Yueting Chou, Chesterfield; David A. Martin, Ballwin, both of Mo.

[73] Assignee: Monsanto Company, St. Louis, Mo.

[21] Appl. No.: 903,305

[22] Filed: Jun. 24, 1992

[51] Int. Cl.$^5$ .............................................. C07C 69/76
[52] U.S. Cl. ..................................... 560/109; 568/31; 568/33; 568/77
[58] Field of Search ................... 560/109; 568/37, 33, 568/77

[56] References Cited

U.S. PATENT DOCUMENTS 4,535,108  8/1985  Rosenquist et al. ................. 524/162
4,908,474  3/1990  Sankey et al. ....................... 560/109

FOREIGN PATENT DOCUMENTS 0390251  3/1990  European Pat. Off. .

Primary Examiner—José G. Dees
Assistant Examiner—Deborah D. Carr
Attorney, Agent, or Firm—R. C. Loyer

[57] ABSTRACT

There is disclosed a process for preparing granular esters in one step by the reaction of an alcohol with acid chloride in an aqueous alkaline medium with moderate shear agitation and optionally in the presence of a surfactant.

18 Claims, No Drawings

PREPARING GRANULAR ESTERS

The present invention relates to the preparation of esters and more particularly to processes whereby said esters are prepared in granular form without the aid of binders.

BACKGROUND OF THE INVENTION

It has long been known that when acid chloride is allowed to react in an aqueous, alkaline mixture with an alcohol, an ester is produced. This known reaction was first investigated and applied by Lossen as reported in Ann. Vol 161, 347 (1872) and 265, 129 (1891) and then by Baumann, Ber. 19 3218 (1886) and Schotten, Ber. 17 2544 (1884). The reaction has received great attention, particularly for the production of benzoyl oxybenzene sulfonate salts. A detailed investigation of what has become known as the "Schotten-Bauman reaction" was published by F. A. Menalda, Rec. Trav. Chim. 49, 967–995 (1930). In this definitive study of the Schotten-Bauman reaction the simultaneous reactions of hydrolysis and alcoholysis of the acid chloride were studied. Menalda reported the effect, in the Schotten-Baumann reaction, of temperature, the nature of the acid chloride, the concentration and nature of the alcohol and the concentration and nature of the alkali. From the results of his experiments, Menalda concluded as follows:
1. The reaction between an alcohol and an acid chloride in aqueous solution should be carried out at the lowest possible temperature, since this is most favorable for high yields of ester. The reaction mixture should be cooled during the reaction to prevent any rise in temperature due to the heat of the reaction.
2. Since the concentrated alcoholic solutions afford higher yields of ester the immediate dilution of the solution with the entire amount of alkali necessary for the reaction is unwarranted, alkali and acid chloride should be added alternately in portions.
3. The use of caustic potash rather than caustic soda is to be recommended, since potassium hydroxide affords better yields of este than sodium hydroxide.

Various uses of benzoyl oxybenzene sulfonate salts have been found through the years and a typical utility is reported in U.S. Pat. No. 4,535,108 to Rosenquist et al. According to this patent, the above-mentioned salts are useful as fire retardants in polycarbonates, said utility overcoming the shortcomings of previously employed fire retardants.

With popularization of use of the above-mentioned salts, the Schotten-Baumann reaction was further refined as reported in U.S. Pat. No. 4,908,474 to Sankey et al. A thorough review of the voluminous prior art relating to the Schotten-Bauman reaction is provided in said patent. The Schotten-Baumann reaction is disclosed by Sankey et al to be more efficient when the reaction is conducted with at least equal molar amounts of benzoyl chloride and an alkali metal phenyl sulfonate salt in the presence of a restricted amount of water and base and preferably in the presence of a molar excess of benzoyl chloride. It is further disclosed by Sankey et al that control of the benzoic acid residue in the benzoyl oxybenzene sulfonate salt is achieved by incorporating a small but effective amount of surfactant in the reaction medium.

As was noted by Sankey et al., benzoyl oxybenzene sulfonate salts have received renewed interest in industry because they are useful in bleaching systems. Such systems are most pertinent to the detergent industry and when employed in such industry large amounts of the salt are required. It is therefore desirable to efficiently produce large amounts of benzoyl oxybenene sulfonate salts with a minimum of need for treatment of waste products. Typically, the prior art processes provided benzoyl oxybenzene sulfonate salts in the form of a fine powder which could then be processed, in a second step, into a granular form more suitable for detergent formulations. Typically, binder materials are employed to provide the granular product. A typical example of preparing granular detergent compositions is described in EPO 0 390 251 to Bortolotti et al. A series of steps with high speed and moderate speed granulators is described therein including the use of typical polymers as binder material to convert powder material into the granular form.

Because of the need to reduce undesirable waste products it is important to provide alternative methods which obviate the need for introducing organic materials and to efficiently produce benzoyl oxybenzene sulfonate salts in granular form and in large volume.

SUMMARY OF THE INVENTION

In accordance with this invention there is provided a process for preparing directly, granular esters which comprises the steps of
(a) reacting, in an aqueous alkaline medium, an alcohol with a molar excess of an acid chloride with continuous moderate shearing agitation of the reaction mixture, whereby esters are formed, and
(b) separating the granular ester from the reaction mixture.

Optionally, a small but effective amount of surfactant can be added to the reactor at any stage of the process prior to separation of the product from the reaction mixture. Also, the surfactant may be added in portions at different stages of the process. Thus, as in Sankey et al. noted above, a small, effective amount may be added at the beginning of the reaction. In addition, a portion of the surfactant may be added as in Sankey et al. and additional surfactant added prior to product separation. Alternatively, it is beneficial to add all of the surfactant just prior to separation of the product from the reaction mixture but in sufficient time to allow thorough mixing before separation.

The above-described process provides dense granular esters and particularly alkali metal benzoyl oxybenzene sulfonate salts directly when first formed in the reaction mixture. Optionally, binders may be combined with the granular salt in the reaction mixture to provide more durable particles.

In another aspect of this invention, whether in batch or continuous operation, granular esters are prepared in high yield by providing step-wise addition of an equimolar amount of acid chloride to the reactor, based upon the amount of alcohol, at a uniform rate over the total reaction time of about 2 hours and then adding a slight molar excess of acid chloride at a reduced rate of addition.

In yet another aspect of this invention, it has been discovered that better control of the pH of the reaction mixture and therefore improved control over the possible hydrolysis of reactant is achieved by adding base in portions or continuously during the reaction rather than supplying the total amount of base at the beginning of the reaction. Control of the pH of the reaction mixture at about 10 has been found to be most advantageous in reducing hydrolysis yet providing for an efficient reaction to produce the desired ester.

Because of the great interest in benzoyl oxybenzene sulfonate the invention will be further explained in detail with respect to said product.

DETAILED DESCRIPTION OF THE INVENTION

In accordance with this invention, it has been discovered that granular esters such as benzoyl oxybenzene sulfonate can be produced directly as synthesized in an aqueous alkaline reaction medium. Because the reactant, acid chloride is usually not very soluble in the aqueous alkaline reaction medium, the reaction mixture has traditionally been subjected to agitation involving a high shear rate. Such processes produce product which is a fine powder. Conventionally, the fine powder is then processed into granular material with binders making it more suitable for use in detergent formulations.

It has now been discovered that granular ester, particularly benzoyl oxybenzene sulfonate salts, may be prepared directly in the operation of the Schotten-Baumann reaction by employing agitation of the reaction mixture limited to a shear rate in the moderate range. The particles of benzoyl oxybenzene sulfonate formed in the reaction mixture will remain in the granular form and can be recovered as such when produced under conditions of moderate shear rate. By "moderate shear rate" is meant an impeller tip speed in the range of from about 400 ft./min. to about 1000 ft./min. Typical agitators useful in the operation of the process of this invention include flat blade, turbine types having a 45° angle or, more preferably, hydrofoil type impellers operated so as to provide a tip speed in the above noted range. More particularly, tip speeds, in the range of from about 500 ft./min. to about 900 ft./min. employing hydrofoil type impellers, are preferred.

The reaction medium is prepared as has been practiced in the prior art operation of the Schotten-Baumann reaction with a few exceptions. First, not all of the base is added to the reaction mixture at the beginning of the reaction. It has been found that excellent yields of product are provided and less benzoyl chloride is required by withholding a portion of the required amount of base and then adding base during the reaction to control the pH of the reaction mixture in the range of from about 9.8 to about 10.2, optimally at about 10.0.

It has also been discovered that the benzoyl chloride addition rate affects the product yield and is therefore controlled such that an equimolar amount, in relation to the alkali metal phenol sulfonate, is added to the reaction mixture at a constant rate so as to provide complete addition in about 2 hours. It has been found that increased yield of product is provided in accordance with this invention by adding a slight molar excess of benzoyl chloride to the reaction mixture but at a reduced rate of addition compared to the addition of the initial, equimolar amount. By the term "slight molar excess" is meant from 0.01 to about 0.04 moles of benzoyl chloride in excess of an equimolar amount provided to the reaction mixture. However, the excess amount is added at an addition rate of less than 40% and preferably less than 30% of the rate of addition of the equimolar amount. Excellent results have been achieved when the molar excess of benzoyl chloride is added to the reaction vessel at a rate of only 20% of the addition rate of the equimolar amount. The excess benzoyl chloride is usually added to be reaction mixture over a period of about 20 to 30 minutes. As has been noted herein, the control of the pH of the reaction mixture is achieved by periodic or continuous addition of base to the reaction mixture rather than adding all of the required base at the beginning of the reaction. Employing a constant monitor of the pH of the reaction mixture allows one to control base addition so as to maintain a pH of about 10 throughout the reaction. It has been found that rapid addition of the excess benzoyl chloride renders control of pH at the desired level more difficult.

To provide mild shear rate of the reaction mixture it has been found that impellers having an angle of 45° provide sufficient agitation of the reaction mixture yet allows the benzoyl oxybenzene sulfonate produced thereby to remain in granular form. Previously, it was desired to agitate the reaction mixture at high shear rate to provide an efficient reaction rate and impellers having as high as 90° have been used resulting in the production of a product having the consistency of a fine powder.

It has been found that the benzoyl oxybenzene sulfonate salts formed in accordance with the process of this invention initially are provided in platelet form which, when mixed together under conditions of mild shear rate, agglomerate in the reactor as they are formed. A more severe shear rate prevents the agglomerates from forming or breaks them apart should any form, thereby producing a fine powder rather than the desired granular form.

After completion of the addition of benzoyl chloride, the reaction mixture is held in the reactor for an additional period of time to complete the reaction. The reaction is usually complete within about 1 hour after completion of the addition of benzoyl chloride during which time agitation with moderate shear rate is continued.

It has been found beneficial in the process of this invention to employ a small but effective amount of surfactant in the reaction mixture. A small but desirable increase in product yield is observed when a surfactant is added at the beginning of the reaction or before addition of benzoyl chloride. The product is obtained in more pure form when surfactant is added and well distributed throughout the reaction mixture at any time prior to separation of the granular product from the reaction mixture. The addition of surfactant enables the removal of greater amounts of water during dewatering steps such as filtration or centrifugation. It is well known that sodium chloride is produced as a by-product in the Schotten-Baumann type reaction. This by-product is very soluble in water but, because the benzoyl oxybenzene sulfonate salt is also fairly soluble in water, removal of sodium chloride by water wash results in significant yield losses. Optimum removal of sodium chloride by removal of the reaction medium without washing with water provides high yield of the most pure product.

In one embodiment of this invention, a small amount of surfactant is added with the alkali metal phenol sulfonate salt as noted above. Then, additional surfactant is added in an amount approximately double the amount initially added at about twenty minutes prior to the end of the reaction. Timing of surfactant addition is not critical and the addition of the surfactant can be performed at any time prior to product separation provided it is adequately dispersed throughout the reaction mixture. Total surfactant employed in accordance with this invention is in the range of from about 0.1% to about 0.5% by weight of the reaction mixture. Preferably, the amount of surfactant in the reaction mixture is in the range of from about 0.2% to about 0.4% by weight of the reaction mixture. Excess surfactant results in producing a material which is tacky and less granular. Accordingly, the amount of surfactant should be regulated so as to provide mostly granular material.

After thorough mixing of the surfactant in the reaction mixture, the reaction mixture is separated by conventional means such as vacuum filtration or by centrifuge. The reaction mixture at the end of the process is a slurry easily filtered. Separation of the granular benzoyl oxybenzene sulfonate from the reaction medium should not be unduly delayed as there is a tendency of the granules to break apart and disperse in the reaction medium if left for a considerable period of time, for example in the range of from 6 to 12 hours. However, it has also been found that the granular benzoyl oxybenzene sulfonate salt is less frangible when surfactant is employed in accordance with this invention.

Surfactants employed in the process of this invention are those which do not adversely affect the stability of the granulates in storage or in use as part of a bleach system. Typical anionic surfactants include salts of long-chain ($C_6$–$C_{22}$) monoalkyl sulfuric acid esters (alcohol sulfates), fatty alcohol sulfates, and particularly fatty alcohols with ethylene oxide.

The granules can be air dried at room temperature or subjected to typical drying operations such as vacuum ovens or fluid bed dryers. Typical drying temperatures for a fluid bed dryer can be in the range of about 70° C. 120° C. at the inlet air temperature with a drying time of from 20 to 30 minutes.

The frangibility of the granules relates to the particle strength. The strength of the particle is indicated by a low amount of frangibility. Particles of low frangibility are desired to prevent fracturing of particles during mixing, handling and transporting the material and in forming the detergent formulations. Frangibility is determined by placing 100 grams of the product on a 60 mesh screen. Three rubber balls about 2 inches (5.08 cm) in diameter are placed on the screen. The screen is placed on a ROTAP sieve shaker (manufactured by W. S. Tyler, Inc.) and shaken for 30 minutes. The amount of material which passed through the 60 mesh screen is weighed, and the percent by weight of the sample is calculated. Values below 10% are acceptable.

Optionally, binders may be added to the reaction mixture to provide granular particles having lower frangibility. Typically, binders which can be employed are water soluble organic polymers, starch, agar, xanthane, carboxymethylcellulose, methyl cellulose, polyvinyl pyrrolidone or mixtures of such substances and polymeric carboxylic acids such as polymers of maleic acid, crotonic acid, acrylic acid, maleic acid, polyacrylates, polyvinyl alcohol, copolymers such as crotonic acid/vinyl acetate copolymer (molar ratio 1:10 to 1:80) and maleic acid-acrylic acid copolymers (molar ratio 1:5 to 5:1) such as the copoylmer sold under the trademark Sokolan Registered TM CP-5. In operation, the binder is added to the reaction mixture at any stage of the process prior to separation of the product. It is preferred to add the binder prior to initiation of the reaction or it can be added in portions during the reaction. The binder is mixed thoroughly in the reaction mixture to allow the binder to coat the granular material and solidify upon drying.

While any alkali metal phenol sulfonate salt may be employed such as sodium, lithium or potassium as a starting material, the use of the sodium salt in detergent applications has been found to be most efficient.

In another aspect of this invention, it has been discovered that granules prepared in accordance with the process of this invention possess improved dissolution rate. Granules produced by the process of this invention have provided T90 dissolution rates of less than one minute.

Other typical esters which can be prepared in accordance with this invention include alkyl and aryl esters as illustrated by the following reactions. In each reaction sodium chloride and water are produced as a by-product but is not shown.

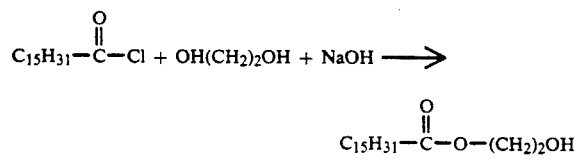

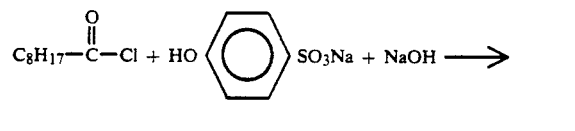

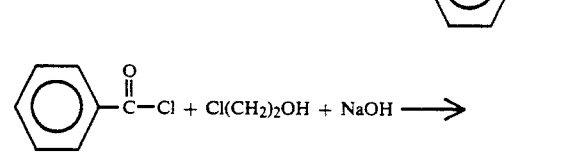

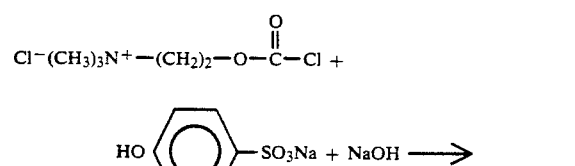

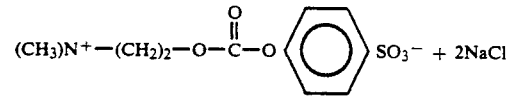

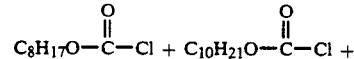

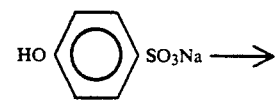

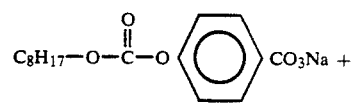

-continued

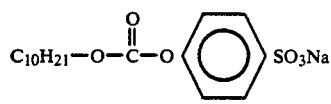

The following examples are for illustrative purposes only and are not intended to limit the scope of this invention in any manner. Unless otherwise stated, all percentages are percent by weight in the following examples.

EXAMPLE 1
Prior Art

A one-liter jacketed and baffled reactor was equipped with an overhead mechanical stirrer (two sets of three blades, turbine type propeller), a thermometer and a pH probe. To this reactor was added 650 cc water, and 232 g sodium phenol sulfonate dihydrate. A slurry was formed and the pH was recorded. To the slurry was added 50% caustic (76.6 g) until the pH reached 10. Cooling circulation began after the caustic addition. When the solution was at 10° C., 140.6 g benzoyl chloride was fed into the reactor through a lab pump, and the system was under a vigorous agitation (1000 rpm). The benzoyl chloride was charged with a constant rate of 70.3 g/hr. During benzoyl chloride addition, the pH was maintained between 10.0-10.3 by adding 10% caustic, and the temperature was controlled at 10° C.

After the addition, the slurry was held at 10° C. for 60 minutes to complete the reaction. The slurry was filtered at around 15° C. through a fritted disc filter under house vacuum. The wet cake loss on drying was 43.7%. The wet cake was transferred to a tray and air dried overnight. The solid was further dried in a vacuum for four more hours at 100° C. About 290.4 g dry product was obtained. The benzoyl oxybenzene sulfonate assay was 95.3% and the chemical yield was 92.2%.

This example demonstrates the prior art method whereby the product is produced in the form of a powder which can be granulated by typical prior art means.

EXAMPLE 2

To a reactor as described in Example was added 650 cc water, 1.0 g Shell Neodol 91-2.5 nonionic surfactant, and 232 g sodium phenol sulfonate dihydrate. A slurry was formed and the pH was recorded. To the slurry was added 50% caustic (76.6 g) until the pH reached 10. Cooling circulation began after the caustic addition. When the solution was at 10° C., 140.6 g benzoyl chloride was fed into the reactor through a lab pump, and the system was under a vigorous agitation (1000 rpm). The benzoyl chloride was charged with a constant rate of 70.3 g/hr. During benzoyl chloride addition, the pH was maintained between 10.0-10.3 by adding 10% caustic, and the temperature was controlled at 10° C.

After the addition, the slurry was held at 10 C for 60 minutes to complete the reaction. The slurry was filtered at around 15° C. through a fritted disc filter under house vacuum. The wet cake LOD was 21.9%. The wet cake was transferred to a tray and air dried overnight. The solid was further dried in a vacuum oven for four more hours at 100°0 C. About 287.9 g dry product was obtained. The benzoyl oxybenzene sulfonate assay was 98.73% and the chemical yield was 94.6%.

This example demonstrates the increased removal of water from the product as indicated by the loss on drying (LOD) when employing surfactant in the reaction mixture. The procedure is comparable to Example 1 with the exception of the addition of surfactant.

EXAMPLE 3

To a reactor as described in Example 1 was added 650 cc water, 1.0 g Shell Neodol 91-2.5 surfactant, and 232 g sodium phenol sulfonate dihydrate. A slurry was formed and the pH was recorded. To the slurry was added 50% caustic (76.6 g) until the pH reached 10. Cooling circulation began after the caustic addition. When the solution was at 10° C., 144.8 g benzoyl chloride was fed into the reactor through a lab pump, and the system was under a vigorous agitation (1000 rpm). The first 140.6 g of benzoyl chloride was charged with a constant rate of 70.3 g/hr. The last 4.2 g (3 molar %) was charged with a slower rate of 9.6 g/hr. During benzoyl chloride addition, the pH was maintained between 10.0-10.3 by adding 10% caustic, and the temperature was controlled at 10° C.

After the addition, the slurry was held at 10°0 C. for 60 minutes to complete the reaction. The slurry was filtered at around 15° C. through a fritted disc filter under house vacuum. The wet cake LOD was 24.7%. The benzoyl oxybenzene sulfonate wet cake was transferred to a tray and air dried overnight. The solid was further dried in a vacuum oven for four more hours at 100° C. About 303.8 g dry product was obtained. The product assay was 97.8% and the chemical yield was 99.0%.

This example demonstrates the increased yield obtained the addition of a slight molar excess of benzoyl chloride delivered to the reaction mixture at a relatively slow rate.

EXAMPLE 4

Into a 4 liter jacketed reactor equipped with 2 baffles and an overhead agitator including 2 sets of A-310 type impellers were charged 1900 cc water, 252 g of 50% sodium hydroxide and 696 g of sodium phenol sulfonate (dihydrate). The mixture was agitated and cooled to a temperature in the range of from about 10°0 to 15° C. There was then added 3 g of Neodol 91-2.5 surfactant in 50 cc water. The temperature was lowered to 10° C. and 422 g of benzoyl chloride were continuously pumped into the reactor over a period of 2 hours. During the feeding time the agitator was adjusted to 800 rpm and the temperature maintained at 10° C. by cooling. Also, the pH of the reaction mixture was maintained in a narrow range of from 10.05 to 10.25 by addition of a 10% solution of sodium hydroxide. After the addition of the above-mentioned amount of benzoyl chloride an additional 13.5 g, representing a 3 molar percent excess, was added to the reaction mixture over a period of about 20-30 minutes which was at a much slower rate than the previous amount. During the slow addition reaction conditions were kept constant at the above temperature and pH ranges. After adding the excess benzoyl chloride the reaction mixture was continuously agitated for an additional one hour without cooling. About 20 minutes prior to the end of the hour an additional 6 g of Neodol 91-2.5 surfactant was added. The slurry in the reactor was warmed to a temperature in the range of 15°-20° C. and filtered through a Buchner funnel. Any lumpy material observed was pushed through a 10 mesh (U.S. standard) screen. The wet granules were dried in a fluid bed dryer at 70° C. for 25 minutes. Granular material having a desirable particle size range of from −10 to +60 constituted about 90% of the recovered material. The yield of benzoyl oxybenzene sulfonate salt, based upon the sodium phenol sulfonate concentration was in the range of from 96–97%. The dried granules contained 0.32% sodium phenol sulfonate, 0.65% sodium benzoate, 2.78% sodium chloride, and 96.42% sodium benzoyl oxybenzene sulfonate. The dried product exhibited a T90 dissolution rate of 0.9 minutes and frangibility of 9.4%.

This example indicates that granular material in high yield is produced directly by means of the Schotten-Baumann reaction without the aid of traditional binders.

EXAMPLE 5

To a 4 liter jacketed reactor which was equipped with two baffles and an overhead agitator with two sets of hydrafoil type impellers, (A-310 type) were charged 1,830 cc of water, 225 g of 50% sodium hydroxide and 696 g of sodium phenol sulfonate (dihydrate). The mixture was agitated and cooled. At 10°-15° C., 3 g of Neodol 91-2.5 surfactant was added and then 540 g of Nacryl BE50, in 50% aqueous solution (a mixture containing 135 g of sorbitol and 135 g of a co-polymer), a binder marketed by National Starch Corporation, was charged. At this point 34.7 g of additional 50% sodium hydroxide was added to bring the pH of the reaction mixture to 10.25. The temperature was adjusted to 10° C. and 422 g of benzoyl chloride was pumped into the system in two hours. During this time agitation was accomplished by means of a 2.5 in. diameter hydrofoil impeller sold by Lightning Mixers under the trade name A-310 driven at 800 rpm while the temperature of the reaction mixture was maintained at or within 1 degree of 10° C. The pH of the reaction mixture was maintained in the range of 10.05 to 10.25 by addition of 10% sodium hydroxide solution. Then, 13.5 g of excess benzoyl chloride (3 mole percent) was added over a period of from 20–30 minutes at a much slower rate than the previous 422 g. During the slow addition, agitation speed, pH and the temperature range were controlled as before. The reaction mixture was held for one hour after additions were made with continued agitation after which cooling was discontinued. The slurry was allowed to warm to a temperature in the range of from 15°C.–20°0 C. and then filtered through a Buchner funnel under house vacuum. The wet cake was scraped off the filter and pushed through a 10 mesh screen (U.S. standard series) and dried. The screened material was dried in a fluid bed dryer at 70° C. for 25 minutes. Upon screening, the dried material consisted of −10 to +60 size granules in 95% yield. Based upon the sodium phenol sulfonate concentration, the yield of pure 4-benzoyl oxybenzene sulfonate was 97.8% and the assay was 88.2% (containing 7.8% binder). The T90 of the product was 2.4 Min.

This example indicates a high yield of granular benzoyl oxybenzene sulfonate with a binder and a minimal amount of surfactant in the reaction mixture.

Other granular esters may be prepared in accordance with the process of this invention by employing other suitable alcohols and acid chlorides.

Although the invention has been described in terms of specific embodiments which are set forth in considerable detail, it should be under stood that this description is by of illustration only and that the invention is not necessarily limited thereto since alternative embodiments and operating techniques will become apparent to those skilled in the art in view of this disclosure. Accordingly, modifications are contemplated which can be made without departing from the spirit of the described invention.

We claim:
1. A process for preparing granular benzoyl oxybenzene sulfonate salts which comprises the steps of
  (a) reacting, in an aqueous alkaline medium, an alkali metal phenol sulfonate with molar excess of benzoyl chloride wherein the benzoyl chloride and at least a portion of the base are added stepwise during the reaction, with continuous moderate shearing agitation of the reaction mixture, and;
  (b) separating the granular benzoyl oxybenzene sulfonate salt from the reaction mixture.
2. The process of claim 1 wherein the alkali phenol sulfonate is sodium phenol sulfonate.
3. The process of claim 12 wherein the sodium phenol sulfonate is hydrated.
4. The process of claim 1 wherein the mole ratio of base to phenol sulfonate is about 1:1.
5. The process of claim 1 wherein the total mole ratio of benzoyl chloride to phenol sulfonate is about 1.03:1 and wherein the rate of addition of said amount of benzoyl chloride up to an equimolar amount is in the range of about 0.5 equivalent per hour and the rate of addition of the molar excess is substantially below said rate.
6. The process of claim 1 wherein a surfactant is added in step (a) in the amount of less than 0.1 percent by weight of the reaction mixture.
7. The process of claim 1 wherein the temperature of the reaction medium in step (a) is maintained in the range of from about 10° C. to about 12° C.
8. The process of claim 1 wherein the pH of the reaction mixture in step (a) is maintained in the range of from about 9.8 to about 10.25 by addition of base during step (a).
9. The process of claim 1 wherein the surfactant is added stepwise, a minor portion thereof being added in step (a) and a major portion being added in step (b), the total amount of surfactant being in the range of from about 0.2 to about 0.3. percent by weight of the reaction mixture.
10. The process of claim 1 wherein the surfactant is an alcohol ethoxylate.
11. The process of claim 1 wherein the shear is provided by a hydrafoil type impeller.
12. The process of claim 11 wherein the tip speed of the impeller is in the range of from about 500 feet per minute to about 900 feet per, minute.
13. The process of claim 1 wherein the shear is provided by a turbine type impeller.
14. The process of claim 13 wherein the impeller tip speed is in the range of from about 400 feet per minute to about 900 feet per minute.
15. The process of claim 11 wherein the particle size of the at least about 95% by weight of the benzoyl 'oxybenzene sulfonate is in the range of from about −10 to about +60 mesh size.
16. The process of 15 wherein the addition rate of the molar excess of benzoyl chloride is less than about 40% of the rate at which the equimolar amount was added.
17. The process of claim 16 wherein the addition rate of the molar excess of benzoyl chloride in about 20% of the rate at which the equimolar amount was added.
18. The process of claim 1 wherein the surfactant is added in step (b) in an amount in the range of from about 0.1% to about 0.2% by weight of the reaction mixture.

* * * * *